(12) United States Patent
Piantoni et al.

(10) Patent No.: US 8,097,298 B2
(45) Date of Patent: Jan. 17, 2012

(54) METHOD FOR PRODUCING DIAPER COMPONENT PARTS FROM STRIP MATERIAL

(75) Inventors: Matteo Piantoni, Albino (IT); Luca Aiolfi, Izano (IT); Alberto Perego, Milan (IT); Robert Perneborn, Göteborg (SE); Marcus Lehto, Fotö (SE); Anders Norder, Lindome (SE)

(73) Assignee: GDM S.p.A., Bologna (IT)

( * ) Notice: Subject to any disclaimer, the term of this patent is extended or adjusted under 35 U.S.C. 154(b) by 203 days.

(21) Appl. No.: 12/524,527

(22) PCT Filed: Jan. 23, 2008

(86) PCT No.: PCT/IB2008/000148
§ 371 (c)(1),
(2), (4) Date: Jul. 24, 2009

(87) PCT Pub. No.: WO2008/090449
PCT Pub. Date: Jul. 31, 2008

(65) Prior Publication Data
US 2010/0112202 A1  May 6, 2010

(30) Foreign Application Priority Data
Jan. 24, 2007  (IT) ............................... B02007A0040

(51) Int. Cl.
*B05D 5/10* (2006.01)

(52) U.S. Cl. .................. 427/207.1; 427/208; 427/289; 156/205; 156/214
(58) Field of Classification Search ............... 427/207.1, 427/208, 289; 156/205, 214
See application file for complete search history.

(56) References Cited

U.S. PATENT DOCUMENTS

| | | | |
|---|---|---|---|
| 3,556,510 A * | 1/1971 | Treff | 270/52.07 |
| 5,556,504 A | 9/1996 | Rajala et al. | |
| 5,779,689 A | 7/1998 | Pfeifer et al. | |
| 6,139,004 A | 10/2000 | Couillard et al. | |
| 6,269,720 B1 * | 8/2001 | Pelagatti | 83/343 |
| 6,440,239 B1 | 8/2002 | Vogt | |
| 2004/0077473 A1 * | 4/2004 | Kubalek et al. | 493/346 |
| 2004/0159075 A1 * | 8/2004 | Matthews | 53/412 |
| 2006/0004333 A1 | 1/2006 | Olson | |

* cited by examiner

*Primary Examiner* — Michael Cleveland
*Assistant Examiner* — Xiao Zhao
(74) *Attorney, Agent, or Firm* — Marshall, Gerstein & Borun LLP

(57) ABSTRACT

A method for producing diaper component parts (3) from strip material (5, 8), wherein the strip material (5, 8) is fed continuously, by means of conveying means (6), along a straight path (P) extending through a number of work stations (9, 16, 21) synchronized with one another; and wherein, along the path (P), the strip material (5, 8) is secured to the conveying means (6) so that all points of the strip material (5, 8) travel at the same speed.

11 Claims, 1 Drawing Sheet

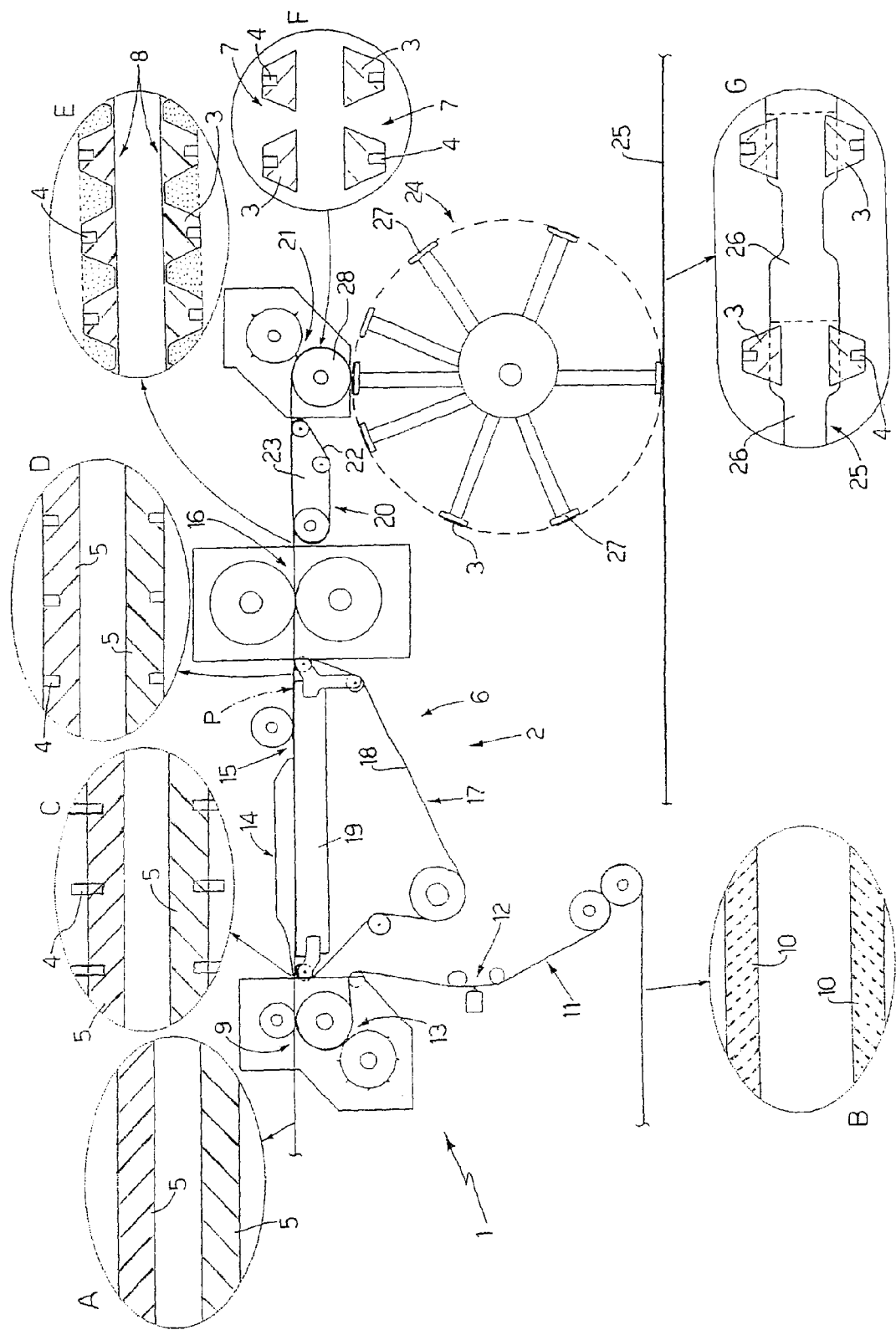

METHOD FOR PRODUCING DIAPER COMPONENT PARTS FROM STRIP MATERIAL

CROSS-REFERENCE TO RELATED APPLICATIONS

This application is the U.S. national phase application of PCT/IB2008/000148, filed Jan. 23, 2008, which claims the benefit of Italian patent application No. BO 2007A 000040, filed Jan. 24, 2007.

TECHNICAL FIELD

The present invention relates to a method for producing diaper component parts from strip material.

BACKGROUND ART

In the diaper industry, diapers are made from a continuous strip of flat unfinished diaper blanks; finish component parts, normally of elastic material, are applied to the strip; and the strip is cut crosswise into a succession of flat finished diapers.

More specifically, one of the finish component parts comprises lateral panels, which have a portion of adhesive or Velcro-type material, and are applied to the sides of each diaper blank to connect the ends of the diaper, when worn, into an annular belt.

The lateral panels—to which the following description refers purely by way of example—are normally formed from a continuous strip of elastic material which is fed along a path, extending through a number of work stations, by conveying means normally defined by conveyor rollers, about which the strip is partly wound.

Though effective and widely used on diaper manufacturing machines, the above method has several drawbacks, on account of the irregular shape of the path, the pull exerted on the strip by the conveyor rollers, and the stress to which the strip is subjected at the work stations, resulting in increasing and decreasing tension of the strip as it travels along the path, and, given the elasticity of the strip material, in inevitable uncontrolled slippage of the material.

Because the work stations are synchronized with one another and the strip must be maintained in a predetermined position, as it travels along the path, to ensure it is positioned correctly on entering each work station, provision is made, along the path, for position sensors, and compensating stations connected to the sensors to correct any variation in the tension of the material and so prevent the strip from deviating from the correct position.

The sensors and compensating stations obviously complicate the machine mechanically, thus impairing reliability and greatly increasing the cost and overall size of the machine.

Though to a lesser degree, the above problem is also encountered when using strip material that is not exactly elastic and visibly stretchable, but nevertheless has a certain degree of intrinsic elasticity.

DISCLOSURE OF INVENTION

It is an object of the present invention to provide a method for producing diaper component parts from strip material, which is cheap and easy to implement, and provides for eliminating the aforementioned drawbacks.

According to the present invention, there is provided a method for producing diaper component parts from strip material, as claimed in claim 1 and, preferably, in any one of the following Claims depending directly or indirectly on claim 1.

BRIEF DESCRIPTION OF THE DRAWING

A non-limiting embodiment of the present invention will be described by way of example with reference to the attached drawing, which shows a schematic side view of a diaper manufacturing machine implementing the method according to the present invention.

BEST MODE FOR CARRYING OUT THE INVENTION

Number 1 in the attached drawing indicates as a whole a diaper manufacturing machine comprising a unit 2 for producing component parts 3 from elastic strip material. The term "elastic" is intended to mean both strip material that is visibly stretchable, i.e. to the naked eye, and strip material that is not visibly stretchable but nevertheless has a certain degree of intrinsic elasticity.

In the example shown, component parts 3 are defined by elastic panels, which have respective bands 4 of adhesive material, glue or Velcro, and are located, in the finished diaper, on either side of a rear longitudinal end (in the drawing) and/or front longitudinal end (not shown) of the diaper to connect the ends of the diaper, when worn, into an elastic annular belt.

As shown in the drawing, the elastic strip material from which component parts 3 are formed is fed to unit 2 in the form of two continuous parallel strips 5 (detail A), and is fed by conveying means 6 along a straight path P extending through a number of work stations to obtain a respective line 7 of aligned component parts 3 from each strip 5.

More specifically, at its input, unit 2 comprises an application station 9 for applying bands 4 to strips 5, and which in turn comprises two counter-rotating rollers located on opposite sides of path P, with their respective axes crosswise to path P, and which between them define a channel for the passage of strips 5. One of the two rollers is a suction roller and deposits the pregummed bands 4 successively, with a given spacing, along one edge of each strip 5, so that bands 4 project transversely outwards from each strip 5, on the opposite side to the other strip 5 (as shown in detail C).

Bands 4 are formed from two strips 10 of adhesive or Velcro-type material (detail B) which are fed, parallel to each other and by a feed line 11, through a gumming station 12, and a cutting station 13 where a knife, cooperating with the suction roller at application station 9, cuts the two strips 10 crosswise to form respective successions of individual bands 4 on the suction roller.

A folding station 14, for folding bands 4, is located downstream from application station 9 in the travelling direction of strips 5 along path P, and comprises two fixed helical folding devices located on opposite sides of the whole defined by the two strips 5, and which, as strips 5 travel past, intercept bands 4 to fold each band 4 into a U onto a top surface of relative strip 5.

The downfolded position of bands 4 is stabilized at a follow-up pressing station 15 comprising a pressure roller, positioned across path P to press bands 4 on relative strips 5 as strips 5 travel under the roller (detail D).

At a forming station 16, downstream from pressing station 15 along path P, strips 5 are fed through a cutting device and cut into substantially trapezoidal shapes to form respective continuous strips 8 of component parts 3, each, having a respective band 4 located in the centre of the respective minor base (detail E).

Strips 5 are fed between application station 9 and forming station 16 by a belt conveyor 17, which forms part of conveying means 6 and comprises an endless belt 18 permeable to air and wound partly about a number of pulleys defining, on the belt, a straight work branch travelling at a linear speed v and coincident with the relative portion of path P between application station 9 and forming station 16.

Belt conveyor 17 also comprises a suction chamber connected to a suction circuit (not shown) and extending beneath the work branch to grip strips 5 by suction onto the work branch from the output of application station 9 and through folding station 14 and pressing station 15 to the input of forming station 16.

Conveying means 6 comprise a further belt conveyor 20 similar to belt conveyor 17 and extending from the output of forming station 16 to a cutting station 21 where continuous strips 8 of component parts 3 are cut crosswise into lines 7 of separate component parts 3 (detail F).

Like belt conveyor 17, belt conveyor 20 comprises a belt 22 permeable to air and wound partly about a number of pulleys defining, on belt 22, a straight work branch coincident with the relative portion of path P and travelling at the same linear speed v as the work branch of conveyor 17.

Inside belt conveyor 20, a suction chamber 23, connected to a suction circuit (not shown), communicates with the bottom surface of the work branch of belt 22 to grip continuous strips 8 of component parts 3 onto belt 22 as strips 8 travel from forming station 16 to cutting station 21.

Belt conveyors 17 and 20 are synchronized with the work stations so that strips 5 and strips 8—which, being gripped by suction to belt conveyors 17 and 20, also travel at linear speed v—are fed through respective forming and cutting stations 16 and 21 in time with operation of the work stations.

At the output of unit 2, machine 1 comprises a transfer device 24 for transferring the component parts in lines 7 in pairs onto a strip 25 defined by a continuous succession of flat diaper blanks 26, so as to apply the component parts 3 in each pair to either side of one end of a respective blank 26 (detail G).

Transfer device 24 comprises a number of arms with respective suction gripping heads 27, which travel along a circular path to pick respective pairs of side by side component parts 3 off a suction drum 28 interposed between cutting station 21 and transfer device 24 to feed lines 7 of component parts 3 continuously to transfer device 24.

Since component parts 3 are normally fed to transfer device 24 at a speed v1, and strip 25 of blanks travels at a speed v2 different from and normally faster than v1, transfer device 24 in the example shown is an accelerating device, in which each gripping head 27 varies its speed cyclically along the circular path to pick up component parts 3 at speed v1, and release component parts 3 onto strip 25 at speed v2.

In other embodiments not shown, speed v1 may be faster than or the same as speed v2. In the former case, gripping heads 27 therefore decelerate cyclically to release component parts 3, and, in the latter case, travel from drum 28 to strip 25, and vice versa, at constant speed.

Operation of machine 1 will be clear from the above description, with no further explanation required.

To conclude, however, it is important to stress the advantages of the method according to the present invention.

By employing a straight path P and suction belt conveyors 17 and 20, all the points along each strip 5 and each strip 8 are subjected to the same tension along path P, so the elastic material undergoes no stretching or slackening between one work station and another, by virtue of being gripped by suction to the work branches of belts 18 and 22, so that each point of the elastic material travels at the same linear speed v as belts 18 and 22.

Using the method according to the present invention, unit 2 therefore needs no position sensors or compensation stations to detect and correct any variation in tension and prevent uncontrolled slippage of the elastic material. As a result, machine 1 is more compact, simpler in design, and therefore more reliable and cheaper.

The invention claimed is:

1. A method for producing diaper component parts (3) from elastic strip material (5); the method comprising:
    feeding the elastic strip material (5) through an application station (9) to receive pregummed bands (4) of adhesive or Velcro-type material, which are spaced along the elastic strip material (5) with a given spacing and project transversely outwards from the elastic strip material (5);
    feeding the elastic strip material (5) through a folding station (14) for folding each band (4) into a U onto a top surface of the elastic strip material (5) and successively through a follow-up pressing station (15) for stabilizing the downfolded position of the bands (4);
    feeding the elastic strip material (5) through a forming station (16) for cutting the elastic strip material (5) into the shape of said component parts (3) to form, from the elastic strip material (5), a continuous strips (8) of component parts (3), each having a respective band (4);
    feeding the continuous strips (8) of component parts (3) through a cutting station (21) for cutting the continuous strips (8) of component parts (3) into separate component parts (3) which can be successively applied to flat diaper blanks (26);
    feeding the elastic strip material (5) continuously between the application station (9) and the forming station (16) and feeding the continuous strips (8) of component parts (3) continuously between the forming station (16) and the cutting station (21) by means of conveying means (6) defining a straight path (P) extending through the stations (9, 14, 15, 16, 21); and
    securing the elastic strip material (5) and the continuous strips (8) of component parts (3) to the conveying means (6) by suction so that all points of the elastic strip material (5) and of the continuous strips (8) of component parts (3) travel at the same speed.

2. A method as claimed in claim 1, wherein the application station (9) comprises two counter-rotating rollers located on opposite sides of the path (P), with their respective axes crosswise to the path (P), and which between them define a channel for the passage of the elastic strip material (5).

3. A method as claimed in claim 2, wherein one of the two rollers is a suction roller and deposits the pregummed bands (4) successively, with a given spacing, along one edge of the elastic strip material (5), so that the bands (4) project transversely outwards from the elastic strip material (5).

4. A method as claimed in claim 3 and comprising:
    feeding an adhesive or Velcro-type strip material (10) through a gumming station (12); and
    feeding the pregummed adhesive or Velcro-type strip material (10) through a cutting station (13) where a knife, cuts the adhesive or Velcro-type strip material (10) crosswise to form a succession of individual bands (4).

5. A method as claimed in claim 4, wherein the knife cooperates with the suction roller at the application station (9)

to cut the adhesive or Velcro-type strip material (10) crosswise to form a succession of individual bands (4) on the suction roller.

6. A method as claimed in claim 1, wherein the folding station (14) comprises a fixed helical folding device which, as the elastic strip material (5) travels past, intercepts the bands (4) to fold each band (4) into a U onto a top surface of the elastic strip material (5).

7. A method as claimed in claim 1, wherein the pressing station (15) comprises a pressure roller which is positioned across the path (P) to press the bands (4) on the elastic strip material (5) as the elastic strip material (5) travels under the pressure roller.

8. A method as claimed in claim 1 and comprising cutting the elastic strip material (5), in the forming station (16), into substantially trapezoidal shapes to form the continuous strips (8) of component parts (3), each having a respective band (4) located in the center of a respective minor base.

9. A method as claimed in claim 1, wherein the conveying means (6) are belt conveying means (17, 20).

10. A method as claimed in claim 1, wherein the conveying means (6) comprises a first suction belt conveyor (17) arranged between the application station (9) and the forming station (16), and a second suction belt conveyor (20) arranged between the forming station (16) and the cutting station (21).

11. A method as claimed in claim 1, wherein the elastic strip material (5) and the continuous strips (8) of component parts (3) are fed onto said path (P) in the form of two continuous side by side strips (5, 8).

\* \* \* \* \*

UNITED STATES PATENT AND TRADEMARK OFFICE
CERTIFICATE OF CORRECTION

PATENT NO. : 8,097,298 B2  
APPLICATION NO. : 12/524527  
DATED : January 17, 2012  
INVENTOR(S) : Matteo Piatoni et al.

Page 1 of 1

It is certified that error appears in the above-identified patent and that said Letters Patent is hereby corrected as shown below:

On the Title Page:

At Item (75), second named inventor, "Izano" should be -- Issano --.

Signed and Sealed this
Twenty-ninth Day of May, 2012

David J. Kappos
*Director of the United States Patent and Trademark Office*